(12) United States Patent
Williams et al.

(10) Patent No.: US 10,933,232 B2
(45) Date of Patent: Mar. 2, 2021

(54) ELECTRICAL APPARATUS AND METHODS AND APPARATUS FOR POSITIONING AND IMPLANTING COMPONENTS THEREOF

(71) Applicant: The Bionics Institute of Australia, East Melbourne (AU)

(72) Inventors: Christopher Edward Williams, East Melbourne (AU); Joel Villalobos Villa, East Melbourne (AU); Owen Burns, East Melbourne (AU)

(73) Assignee: The Bionics Institute of Australia, East Melbourne (AU)

( * ) Notice: Subject to any disclaimer, the term of this patent is extended or adjusted under 35 U.S.C. 154(b) by 72 days.

(21) Appl. No.: 16/045,311

(22) Filed: Jul. 25, 2018

(65) Prior Publication Data

US 2019/0134381 A1    May 9, 2019

Related U.S. Application Data

(63) Continuation of application No. 14/424,393, filed as application No. PCT/AU2013/000960 on Aug. 28, 2013, now Pat. No. 10,058,700.
(Continued)

(30) Foreign Application Priority Data

Aug. 29, 2012    (AU) ............................... 2012903745

(51) Int. Cl.
  *A61N 1/05*    (2006.01)
  *A61B 5/00*    (2006.01)
  (Continued)

(52) U.S. Cl.
  CPC ........ *A61N 1/0543* (2013.01); *A61B 5/04001* (2013.01); *A61B 5/0496* (2013.01);
  (Continued)

(58) Field of Classification Search
  CPC . A61N 1/0543; A61N 1/36046; A61B 5/6821
  (Continued)

(56) References Cited

U.S. PATENT DOCUMENTS

| 5,107,856 A | 4/1992 | Kristiansen et al. |
| 5,476,493 A | 12/1995 | Muff |

(Continued)

FOREIGN PATENT DOCUMENTS

| JP | H10248941 | 9/1998 |
| WO | WO-2010124321 | 11/2010 |

(Continued)

OTHER PUBLICATIONS

"U.S. Appl. No. 14/424,393, Non Final Office Action dated Sep. 22, 2017", 8 pgs.
(Continued)

*Primary Examiner* — Amanda K Hulbert
*Assistant Examiner* — Philip C Edwards
(74) *Attorney, Agent, or Firm* — Schwegman Lundberg & Woessner, P.A.

(57) ABSTRACT

An anchor device is described that is adapted to support one or more conductors extending out of an opening in an outer surface of an eye, from a device implanted in the eye to a communications interface. The anchor device comprises a conductor receiving portion including a channel, the conductors being positionable through the channel; and a fixation portion connected to the conductor receiving portion, the fixation portion being adapted to be secured to the outer surface of the eye. The conductor receiving portion is configured to allow movement of the channel and/or conductors relative to the fixation portion. A visual prosthesis comprising the anchor device is also described, along with apparatus and methods for positioning the visual prosthesis or other types of implantable electrical apparatus.

21 Claims, 9 Drawing Sheets

Related U.S. Application Data

(60) Provisional application No. 61/694,447, filed on Aug. 29, 2012.

(51) Int. Cl.

| | | |
|---|---|---|
| *A61B 5/04* | (2006.01) | |
| *A61B 5/0496* | (2006.01) | |
| *A61N 1/36* | (2006.01) | |
| *A61N 1/372* | (2006.01) | |

(52) U.S. Cl.
CPC ............ *A61B 5/686* (2013.01); *A61B 5/6821* (2013.01); *A61N 1/36046* (2013.01); *A61N 1/36064* (2013.01); *A61N 1/37211* (2013.01); *A61B 2562/222* (2013.01); *A61N 1/0531* (2013.01)

(58) Field of Classification Search
USPC ........................................................ 600/377
See application file for complete search history.

(56) References Cited

U.S. PATENT DOCUMENTS

| | | | |
|---|---|---|---|
| 6,024,764 A * | 2/2000 | Schroeppel | A61F 2/04 |
| | | | 264/296 |
| 7,218,972 B2 | 5/2007 | Rodriguez | |
| 2004/0176831 A1 | 9/2004 | Gliner et al. | |
| 2006/0259112 A1 | 11/2006 | Greenberg et al. | |
| 2007/0173905 A1 | 7/2007 | Greenberg et al. | |
| 2011/0009935 A1 | 1/2011 | Kane et al. | |
| 2011/0202109 A1 | 8/2011 | Kamei et al. | |
| 2012/0029335 A1 | 2/2012 | Sudam et al. | |
| 2015/0251002 A1 | 9/2015 | Williams et al. | |

FOREIGN PATENT DOCUMENTS

| | | |
|---|---|---|
| WO | WO-2011022773 | 3/2011 |
| WO | WO-2014032096 | 3/2014 |

OTHER PUBLICATIONS

"U.S. Appl. No. 14/424,393, Notice of Allowance dated Apr. 26, 2018", 7 pgs.

"U.S. Appl. No. 14/424,393, Preliminary Amendment filed Jul. 28, 2015", 8 pgs.

"U.S. Appl. No. 14/424,393, Response filed Sep. 6, 2017 to Restriction Requirement dated Aug. 9, 2017", 9 pgs.

"U.S. Appl. No. 14/424,393, Response filed Dec. 19, 2017 to Non Final Office Action dated Sep. 22, 2017", 11 pgs.

"U.S. Appl. No. 14/424,393, Restriction Requirement dated Aug. 9, 2017", 8 pgs.

"European Application Serial No. 13834258.9, Extended European Search Report dated Apr. 14, 2016", 8 pgs.

"European Application Serial No. 13834258.9, Office Action dated Apr. 15, 2015", 3 pgs.

"European Application Serial No. 13834258.9, Response filed Jul. 8, 2015 to Office Action dated Apr. 15, 2015", 13 pgs.

"International Application No. PCT/AU2013/000960, International Search Report and Written Opinion dated Nov. 5, 2013", (Nov. 5, 2013), 14 pgs.

\* cited by examiner

ELECTRICAL APPARATUS AND METHODS AND APPARATUS FOR POSITIONING AND IMPLANTING COMPONENTS THEREOF

CROSS-REFERENCE TO RELATED APPLICATIONS

This application is a continuation of and claims the benefit of priority to U.S. patent application Ser. No. 14/424,393, filed Feb. 26, 2015, which is a U.S. national stage application under 35 U.S.C. § 371 of PCT/AU2013/000960, filed Aug. 28, 2013, and published as WO 2014/032096 on Mar. 6, 2014, and which claims priority to Australian Provisional Patent Application No 2012903745 filed on 29 Aug. 2012, and claims priority to U.S. Provisional Patent Application No. 61/694,447 filed on 29 Aug. 2012, which applications and publication are incorporated by reference as if reproduced herein and made a part hereof in their entirety, and the benefit of priority of each of which is claimed herein.

FIELD

The present patent application relates to electrical apparatus and methods and apparatus for positioning and implanting components of the electrical apparatus.

BACKGROUND

Electrical apparatus that includes implantable components has been developed for a variety of medical purposes. Commonly, the apparatus comprises one or more electrodes that are implanted in or on a target portion of a patient's body. The electrodes can electrically stimulate the body and/or sense electrical activity in the body.

Electrical apparatus has been developed, for example, to restore or improve vision within blind or partially blind patients. A visual prosthesis such as a retinal prosthesis commonly includes an implantable component having an electrode array, situated on or in a substrate, for placement in the eye on or near retinal nerve cells. Electrical signals are transmitted via the electrodes to the retinal nerve cells, triggering a perception of light within the patient's brain. The prosthesis can therefore provide the perception of vision to patients, e.g. whose retinal photoreceptors have become dysfunctional.

Commonly, a visual prosthesis is used in conjunction with a video camera. A stream of images detected by the camera is converted into digital signals by an image processor and electrical signals are applied to the electrodes in accordance with the digital signals.

As another example, apparatus is being developed to diagnose, limit or prevent onset of epileptic seizures. Electrical activity is sensed and/or electrical stimulus is applied, by an implantable component having one or more electrodes placed within or near the source or sources of seizures in the brain. The electrical stimulus is intended to terminate or at least counteract epileptic seizure events arising from those sources.

In both examples, to communicate with the electrodes when the implantable component is located in a target position, a lead can extend from the implantable component and exit the body via an incision. The lead can be connected to a communications interface such as a wireless transmitter/receiver, an electrical connector or an electrical plug socket (e.g. a "pedestal"), located remotely from the implantable component.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to a first aspect, there is provided an anchor device adapted to support one or more conductors extending out of an opening in an outer surface of an eye, from a device implanted in the eye to a communications interface, the anchor device comprising:

a conductor receiving portion including a channel, the conductors being positionable through the channel; and a fixation portion connected to the conductor receiving portion, the fixation portion adapted to be secured to the outer surface of the eye;

wherein the conductor receiving portion is configured to allow movement of the channel relative to the fixation portion.

According to a second aspect, there is provided an anchor device adapted to support one or more conductors extending out of an opening in an outer surface of an eye, from a device implanted in the eye to a communications interface, the anchor device comprising a conductor receiving portion including a channel, the conductors being positionable through the channel; and a fixation portion connected to the conductor receiving portion, the fixation portion adapted to be secured to the outer surface of the eye;

wherein the conductor receiving portion is configured to allow movement of the conductors relative to the fixation portion.

In the preceding aspects, by configuring the conductor receiving portion to allow movement of the channel and/or conductors positioned in the channel, relative to the fixation portion, the fixation portion may be substantially isolated from any movement of the channel and/or movement of the conductors positioned in the channel. The conductors may be considered to "float" to some extent within the anchor device. The anchor device can stabilise the conductors as they extend out of the opening at the outer surface of the eye, while at the same time allowing for a controlled degree of movement of the conductors at or adjacent this location. The arrangement can reduce the possibility that movement of the conductors will unseat the anchor device or cause damage to the eye.

The conductors may be provided in a lead that extend from the device implanted in the eye, through the anchor device, and to the communications interface. The lead may be positionable within the channel of the conductor receiving portion. The lead may be moveable within the channel and/or the lead may be moveable relative to the fixation portion. The lead may be fixed within the channel at a portion of the channel only, e.g. fixed along a length of less than 50%, less than 40% or less than 30% of the channel. The channel may have first and second openings, such that lead can extend from the implanted device through the first opening into the channel and extend through the second opening out of the channel towards the communications interface, and the lead may be fixed at or adjacent one end of the channel only, e.g. the second opening only.

In one embodiment, the anchor device is adapted to locate over the opening in the outer surface of the eye. Therefore, the anchor device may provide support for the one or more conductors at the position that they extend out of the opening in the outer surface of the eye. Furthermore, the anchor device may shield the opening in the outer surface of the eye.

The anchor device may be employed in visual prosthesis apparatus in which the conductors travel from the device implanted in the eye of the patient, out of the opening in outer the surface of the eye, to the communications interface remote from the eye. The device implanted in the eye may include, for example, an array of electrodes configured to apply electrical current to retinal cells of an eye in order to provide the patient with a perception of vision. The array of electrodes may be positioned in or on a substrate, e.g. a flexible substrate.

The communications interface may comprise a wireless transmitter/receiver or comprise an electrical connector (e.g. a plug socket or "pedestal"), allowing for a wired or wireless connection between the implanted device and an electrical component such as a signal generator or otherwise. The communications interface may be directly connected to, or form part of, the electrical component, or may be separate from the electrical component. In one embodiment, the communications interface may comprise a connection point between the conductors and a signal generator such as an implantable signal generator. The communications interface may be attached to, or wholly or partially implanted in, the side of the patient's head, or at another part of the patient's anatomy.

The device implanted in the eye may be a device as described in Applicant's PCT Publication No. WO 2011/022773, for example, the content of which is incorporated herein by reference, or it may be another type of implantable device.

The conductors may extend in a helical and/or wavy configuration through the channel and/or other parts of the visual prosthesis apparatus, such as the device implanted in the eye and/or the lead extending from the anchor device to the communications interface. By using helically configured conductors or conductors with a wavy shape, upon flexing of the apparatus, the conductors can effectively expand or contract in length as necessary, avoiding damage to parts of the apparatus including the conductors themselves.

The fixation portion and the conductor receiving portion may each have a bottom surface for locating on the outer surface of the eye. The bottom surfaces may be substantially flush with each other. The bottom surfaces may be curved to substantially follow the contours of the outer surface of the eye to ensure even contact with the eye when the anchor device is secured to the outer surface of the eye.

In addition to stabilising the conductors adjacent the outer surface of the eye, the anchor device may serve to route the conductors or lead including the conductors in an appropriate direction away from the anchor device and the eye, towards the communications interface, e.g., past extraocular muscles of the eye and towards the lateral orbital rim. To achieve this, the channel within the anchor device may follow a bent path. The channel path may bend by, for example, 45 to 135 degrees. In one embodiment, the channel path may be a substantially right-angled path, i.e. it may bend by about 90 degrees. In another embodiment, the channel path may bend by about 50 to 70 degrees, e.g. about 55 or about 60 degrees. The conductors or lead may be routed from the anchor device along a substantially horizontal path, or may be routed from the anchor device along a path that is angled from horizontal. For example, the path may be angled upwardly from horizontal, e.g. by about 20 to 30 degrees or otherwise. It has been determined that such channel path bends can provide improved routing of the conductors away from the opening in the outer surface of the eye, towards the communications interface, in consideration of both positioning of the communications interface and the locations of anatomical features at or adjacent the eye region, such as the extraocular muscles.

The channel in the conductor receiving portion may extend from a first end of the anchor device adjacent the device implanted in the eye and a second end of the anchor device adjacent the lead that extends to the communications interface. At or adjacent the first end, a first opening of the channel may be provided in the bottom surface of the conductor receiving portion to directly receive the conductors as they extend out of the eye. At or adjacent the second end, a second opening of the channel may be provided where the conductors exit the channel and travel through the lead to the communications interface. Accordingly, the first opening may lie in a surface substantially parallel to the outer surface of the eye whereas the second opening may be lie in a surface substantially normal to the outer surface of the eye.

In one embodiment, the fixation portion may be formed of the same or similar material as the conductor receiving portion. However, in alternative embodiments the conductor receiving portion may be formed of material that has greater flexibility and/or elasticity than the fixation portion, so that it is more adaptable to movement of the conductors and/or lead passing through the channel, while the fixation portion is more suitable for securing to the eye. The fixation portion and/or the conductor receiving portion may comprise a polymeric material, e.g. silicone. In the fixation portion, an additional element may be present which may provide for greater rigidity or inelasticity of the fixation portion, and which may not be present at all, or to the same extent, in the conductor receiving portion. The additional element may form a core of the fixation portion or otherwise. The additional element may be a layer of relatively stiff or rigid material such as a layer of mesh, e.g., a mesh comprising polyethylene terephthalate. In one embodiment, the conductor receiving portion comprises silicone only, and the fixation portion comprises silicone embedded with a polyethylene terephthalate mesh (e.g. a Dacron™ mesh). The provision of the stiffening material in the fixation portion may prevent or limit the possibility of sutures, which may be used to fix the anchor device to the outer surface of the eye, from tearing the anchor device. However, the fixation portion may maintain some degree of flexibility/compliancy, ensuring that the fixation portion can conform more readily to the shape of the outer surface of the eye. This stiffening material may be positioned carefully to allow maximum strain relief (including in the z axis) for the conductors and/or lead as they enter the anchor device.

The channel may be formed in the conductor receiving portion as a direct result of moulding material such as silicone over the conductors or lead comprising the conductors to form the conductor receiving portion. As an alternative approach, the channel may be preformed, with the conductors being passed through the channel after forming.

The conductors may travel through a transition portion between the device implanted in the eye (the implantable device) and the anchor device. For example, the conductors may extend out of a substrate of the implantable device, through a transition lead section, before travelling through the anchor device. The transition portion may be flexible. The length of the transition portion may correspond to a thickness of tissue and/or the depth of the incision between the substrate of the implantable device, at the conductor exit position, and the outer surface of the eye. To achieve flexibility, the transition portion, e.g. the transition lead section, may comprise a cladding material that surrounds the conductors and which is relatively flexible and/or relatively narrow. For example, the transition portion may comprise a flexible polymeric material such as silicone that surrounds the conductors. Additionally or alternatively, the transition portion may have substantially no reinforcement where it is connected to the implantable device, e.g. the substrate of the implantable device. In this regard, the transition portion may have no increase in diameter as it extends from the anchor device to the substrate or it may have a decrease in diameter as it extends from the anchor device to the substrate. By providing a flexible transition portion between the implantable device and the anchor device, the anchor device can be less likely to impede or obstruct implantation of the implantable device. The flexibility of the transition portion may allow for increased relative movement between the anchor device and the implantable device during the implantation process, minimising any potentially damaging forces being transferred from the anchor device to the implantable device via the transition portion.

According to a third aspect, there is provided a lead configured to connect a device implantable in an eye to a communications interface external to the eye, the lead comprising:

a reinforcement device, the reinforcement device having a first end and a second end and being elongated between the first end and the second end, the reinforcement device being adapted to be positioned at or adjacent an orbital bone;

a first lead section connected to the first end of the reinforcement device;

a second lead section connected the second end of the reinforcement device; and one or more conductors, wherein the conductors are connectable to the implantable device and are configured to extend from the implantable device, through the first lead section, the reinforcement device and the second lead section, to the communications interface, wherein the reinforcement device has a greater outer diameter than the first and second lead sections.

The lead according to the third aspect may be employed in visual prosthesis apparatus that comprises the anchor device according to the first or second aspects.

The reinforcement device may have at least one bend region, a first reinforcement section on the implantable device side of the bend region, and a second reinforcement section on the communications interface side of the bend region. A channel may extend through each of these sections and the conductors may extend through the channel. The channel may be provided within a third lead section positioned inside the reinforcement device. The first reinforcement section may have a length of approximately 0.5 to 3 cm, e.g. about 1.2 cm, and/or the second reinforcement section may have a length of approximately 0.2 to 2 cm, e.g. about 0.5 cm. The bend region may maintain an angle between the first and second reinforcement sections of approximately 45° to 90°, or approximately 55° to 70°, or about 63°, for example, or otherwise. The outer diameter of the reinforcement device may be about 1 to 5 mm, e g about 2.5 mm, at the first reinforcement section, the second reinforcement section and/or the bend region. The outer diameter of the lead may be about 0.5 to 3 mm, e g about 1 mm, at the first lead section and/or the second lead section. Smooth or tapering transition regions or 'shoulders' may be provided at one or both ends of the reinforcement device to reduce any trauma that may be caused at the transition between the reinforcement device and the first and second lead sections, when the reinforcement device is located in position. Similarly, a tapering transition region may be provided between the anchor device and adjacent portions of the lead. By providing a more streamlined shape to the apparatus, greater strain relief may be provided.

To secure the reinforcement device in position at the lateral orbital rim, a notch may be formed in the orbital bone. The notch may have a recessed groove arranged to receive at least a portion of the reinforcement device, the groove being formed wider than an access opening to the groove. This can allow the reinforcement device to be press-fit through the opening into the groove, reducing the likelihood that the reinforcement device, when located in the groove, will be displaced from the groove. Nonetheless, adhesive material such as bone cement or a titanium bone plate may also be applied to the notch for extra security.

By employing the reinforcement device having a bend region, the lead can, in effect, be pre-shaped to follow anatomy at the lateral orbital margin. This can make routing of the lead more straightforward and secure. Pre-shaping may involve identification of appropriate 3-dimensional geometry for the lead assembly dependent on the anatomy of different patients. Pre-shaping may include optimisation of the location of the reinforcement device along the length of the lead, and may take into account differences between the left and right eyes to avoid twisting of the lead either between the reinforcement device and the implantable component or between the reinforcement device and the communications interface.

According to a fourth aspect, there is provided visual prosthesis apparatus including a device implantable in an eye, a communications interface, and a lead extending between the implantable device and the communications interface, wherein the lead is pre-shaped to substantially follow the outer surface of the orbital bone at the lateral orbital rim adjacent the eye.

The lead may be pre-shaped by having a substantially fixed bend along its length arranged to locate around the orbital bone at the lateral orbital rim. The fixed bend may be achieved, for example, by employing a reinforcement device, e.g. as described with respect to the third aspect, or by configuring a bend in the cladding of the lead. In the latter case, the bend region of the lead may have the same diameter as other sections of the lead.

According to a fifth aspect, there is provided a method for securing a reinforcement device according to the third aspect to an orbital bone, comprising:

forming a notch in the orbital bone, wherein the notch comprises a recessed groove configured to receive the reinforcement device and an access opening through which the reinforcement device is locatable in the recessed groove, wherein the access opening is narrower than the recessed groove.

In one embodiment, a dummy device may be used to assist with sizing of the notch including the recessed groove and the access opening, which dummy device may have substantially the same shape and dimensions as the reinforcement device, at least at regions of the reinforcement device that are to be located in the notch. The dummy device may be included in a surgical pack, along with one or more of the other items discussed herein, such as the anchor device, reinforcement device, and lead, etc.

According to a sixth aspect, there is provided apparatus for positioning components of a visual prosthesis, the visual prosthesis including a device implantable in an eye, a communications interface, and a lead extending between the implantable device and the communications interface, the apparatus comprising:

an elongate element having a proximal end and a distal end, the distal end being insertable through a first incision in a skin surface of a patient, and movable under tissue towards a patient's eye, and a handle portion releasably attachable to a proximal end region of the elongate element;

wherein the elongate element has a first recess at the distal end adapted to receive the implantable device and a channel extending proximally from the first recess adapted to receive the lead, and wherein the handle includes a second recess adapted to receive the communications interface.

According to a seventh aspect, there is provided a method of positioning components of a visual prosthesis, the visual prosthesis including a device implantable in a patient's eye, a communications interface, and a lead extending between the implantable device and the communications interface, the method comprising:

inserting a distal end of an elongate element through a first skin incision remote from the patient's eye, wherein the elongate element has:

a first recess at the distal end, the implantable device being at least partially located in the first recess, and a lead channel extending proximally from the first recess, the lead being at least partially located in the lead channel, and wherein a handle is releasably attached to a proximal end of the elongate element, the handle including a second recess, the communications interface being at least partially located in the second recess;

moving the distal end of the elongate device under tissue towards the patient's eye;

pushing the distal end of the elongate device out of a second skin incision adjacent the patient's eye;

removing the implantable device from the first recess;

releasing the handle portion from attachment with the elongate element;

removing the communications interface from the second recess; and pulling the elongate element out of the second skin incision.

The apparatus and method of the sixth and seventh aspects may be used in conjunction with visual prosthesis apparatus as described above with respect to preceding aspects. In line with this, the implantable device recess may be configured such that the anchor device described with respect to the preceding aspects is also locatable in the first recess (or located elsewhere in the elongate device) and/or the reinforcement device is located in the lead channel (or located elsewhere in the elongated device). The apparatus and method may be used to locate the implantable device beyond the second skin incision at a position adjacent the patient's eye, e.g. at the lateral orbital margin, so that a surgeon may take hold of the implantable device immediately prior to surgical implantation in the eye. At the same time, the lead may be connected to the implantable device and remain routed under the patient's skin or tissue, along the side of the patient skull, to the first incision, adjacent to which the communications interface may be secured to the skull.

The apparatus and method may employ a dummy element to create a pocket under tissue between the first and second skin incisions prior to moving the elongate element between the first and second skin incisions. The dummy element may have a similar or identical profile (external size and shape) to the elongate element. The dummy element may therefore be used to ensure that the elongate element will be moveable more easily between the incisions.

The elongate element, which may also be referred to as a "trocar" or "trochar" or otherwise, may include a head at its distal end that includes the first recess for the implantable device and an arm extending proximally therefrom that includes the lead channel, wherein the lead channel has an opening at its distal end that opens into the first recess. The head may be substantially wider than the arm. The head, which will provide a leading end of the elongate device when it is inserted under the skin, may have a smooth, streamlined shape to minimise surgical trauma. The streamlined shape may be achieved through the provision of a curved distal edge or tip to the head, through forming the head in a relatively flat configuration and/or by providing smooth shoulder portions that join the head to the arm. The flat configuration of the head may allow the head to maintain a relatively low profile against the skull while under the skin.

To encase the implantable device within the first recess during insertion, a lid may be provided. The lid may attach the head in a press-fit manner. The apparatus may include a key operable to release the lid.

The positioning apparatus may be formed of strong and rigid material, e.g. surgical steel, such as to prevent compressive forces damaging the visual prosthesis apparatus located therein. However, in some embodiments, parts of the positioning apparatus may have flexibility to make navigation of portions of the apparatus under tissue, for example, more straightforward.

The handle may include first and second portions that clamp together on opposite sides of the arm, fixing the position of the handle relative to the arm. The clamping may also be used to retain the communications interface in the second recess. The first and second handle portions may be clamped together using a bolt, clasp or otherwise. A release mechanism may be provided to release the clamping, which release may be performed by hand, e.g. using one hand. The release mechanism may be a nut at the end of a bolt, although alternative approaches are possible.

While the apparatus and method of the sixth and seventh aspects is described in conjunction with a visual prosthesis, the apparatus and method can also be used, mutatis mutandis, with other prosthetic devices employing electrical and implantable components.

Thus, according to an eighth aspect, there is provided positioning apparatus for positioning components of electrical apparatus, the electrical apparatus including a device implantable at a target portion of a patient's body, a communications interface, and a lead extending between the implantable device and the communications interface, the positioning apparatus comprising:

an elongate element having a proximal end and a distal end, the distal end being insertable through a first incision in a surface of a patient, and movable under tissue towards the target position, and a handle portion releasably attachable to a proximal end region of the elongate element;

wherein the elongate element has a first recess at the distal end adapted to receive the implantable device and a channel extending proximally from the first recess adapted to receive the lead, and wherein the handle includes a second recess adapted to receive the communications interface.

Further, according to a ninth aspect, there is provided a method of positioning components of electrical apparatus, the electrical apparatus including a device implantable at a target position in a patient's body, a communications interface, and a lead extending between the implantable device and the communications interface, the method comprising:

inserting a distal end of an elongate element through a first incision remote from the target position, wherein the elongate element has:
- a first recess at the distal end, the implantable device being at least partially located in the first recess, and
- a lead channel extending proximally from the first recess, the lead being at least partially located in the lead channel, and wherein
- a handle is releasably attached to a proximal end of the elongate element, the handle including a second recess, the communications interface being at least partially located in the second recess;

moving the distal end of the elongate device under tissue towards the target position;

pushing the distal end of the elongate device out of a second incision adjacent the target position;

removing the implantable device from the first recess;

releasing the handle portion from attachment with the elongate element;

removing the communications interface from the second recess; and pulling the elongate element out of the second incision.

The apparatus and method of the eighth and ninth aspects may be used, for example, in conjunction with any apparatus that employs an implantable electrical component such as an electrode array, the implantable component having a lead extending therefrom that is adapted to connect the implantable component to a communications interface by extending under body tissue. The electrical component may be provided for the purposes of electrostimulation and/or electrical monitoring. The target position for the implantable component may be in or on a patient's eye or head, or may be elsewhere in the body.

In one embodiment, the electrical apparatus may be adapted to diagnose, limit or prevent onset of epileptic seizures, and/or to monitor body parameters associated with epileptic seizures. The implantable device may include an electrode array that is adapted to be placed within or near the source or sources of seizures in the brain. The electrical stimulus may be applied by the electrodes to terminate or at least counteract epileptic seizure events arising from those sources and/or the electrodes may be used to monitor electrical activity within or near the source or sources of seizures in the brain.

The elongate element can be bent or shaped to a curvature as appropriate for a particular application (e.g. as appropriate for the geometry of the body where components of the electrical apparatus are to be positioned). In the case of the epilepsy procedure, the elongate element can have a curvature matched to the patient's skull in order to minimise surgical trauma to the patient. Whole or parts of the elongate element can be bent, shaped or curved.

The elongate element can be fabricated from a variety of different materials included metal (e.g. stainless steel, titanium, Nitinol™), and/or medical grade plastic (Teflon™, PEEK etc), in order to achieve an appropriate flexibility of the elongate element to allow bending. The elongate element may have different degrees of flexibility in different planes or directions, depending on the desired application of the apparatus. For example, the elongate element may be configured to exhibit relative rigidity when pushed from one end, but exhibit relative flexibility when pushed from a top or bottom face. This may ensure that the elongate element can perform a reliable tunnelling function under tissue, while enabling it to be bent around curved anatomical structures.

The apparatus and method of the sixth to ninth aspects may be used in conjunction with a once-piece implantable device and stimulator system. The communications interface may form part of a signal generator, which is connected to the implantable device during the positioning procedure, rather than being positioned independently and only connected together after implantation, for example. The signal generator may be implantable and the signal generator may be at least partially located, in the second recess

BRIEF DESCRIPTION OF THE DRAWINGS

By way of example only, embodiments are now described with reference to the accompanying drawings, in which:

FIG. 1b shows a variation of the visual prosthesis apparatus of FIG. 1a;

FIGS. 2a and 2b show photographic top and bottom views, respectively, of visual prosthesis apparatus configured generally in accordance with the apparatus of FIG. 1a;

FIG. 10 shows a notch in an orbital bone of the eye socket of FIGS. 5a and 5b configured to receive a reinforcement device of the visual prosthesis apparatus of FIG. 1a;

DETAILED DESCRIPTION OF EMBODIMENTS

Various embodiments of the present disclosure relate to visual prosthesis apparatus that employs conductors configured to extend from a device implanted in an eye to a communications interface remote from the eye. The interface may be a plug pedestal or other type of connector, and may comprise a wireless transmitter/receiver or comprise electrical connections for wired communication. The interface may therefore provide for wired or wireless connection between the implanted device and additional electrical components of the visual prosthesis apparatus, which additional components may be implantable or otherwise. The interface may be attached to, or wholly or partially implanted in, the side of the patient's head (or other part of the patient's anatomy).

Throughout this specification the term "visual prosthesis apparatus" is used to denote apparatus for improving a patient's vision (or at least giving improved "perception" of vision), and will be understood to include devices otherwise known as bionic eyes, artificial eyes, retinal prostheses and retinal stimulators or similar. However, features of the present disclosure may be useable with any type of device implanted in the eye, whether for sight restoration or otherwise, or with entirely different types of implantable devices, including devices adapted to stimulate or monitor brain activity.

Figure 1A:
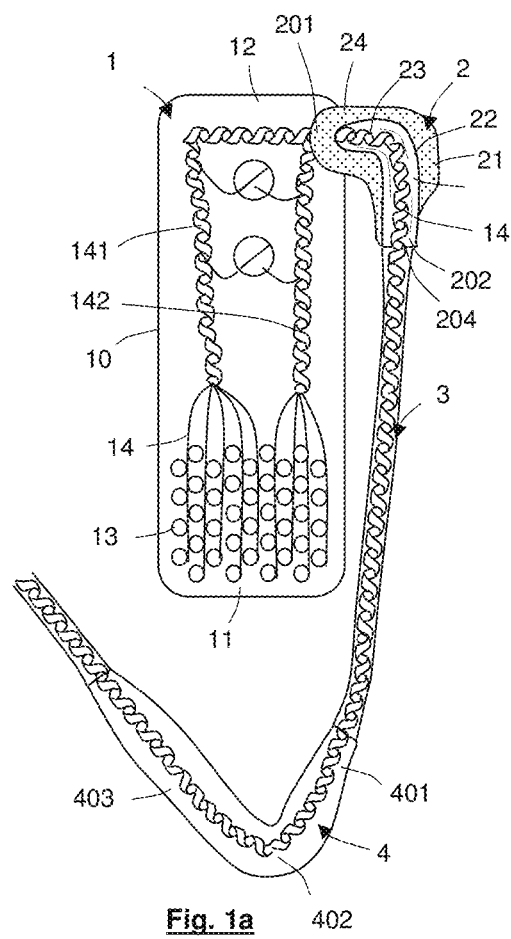
FIG. 1a shows a top view of visual prosthesis apparatus, including an implantable device, an anchor device, and a lead, according to an embodiment of the present disclosure.

FIG. 1a shows a top view of visual prosthesis apparatus according to an embodiment of the present disclosure, the apparatus including an implantable device 1, an anchor device 2 and a lead 3. To further aid understanding, photographic depictions of visual prosthesis apparatus configured generally in accordance with the apparatus of FIG. 1a are provided in FIGS. 2a and 2b, and corresponding reference numerals are used to identify corresponding components for simplicity.

The implantable component 1 has a flexible substrate 10 with a distal end 11 and a proximal end 12. The substrate 10, when viewed from above, is substantially rectangular, with curved corners to minimise surgical trauma, its longitudinal direction extending between the distal and proximal ends 11, 12. Adjacent the distal end 11 of the substrate 10, an array of electrodes 13 is provided for applying electrical current to retinal cells of an eye. Each electrode 13 is connected to a separate electrical conductor, e.g., a biocompatible metal wire 14 such as a platinum wire. As the conductors 14 extend from the electrodes 13 through the substrate 10 towards the proximal end 12 they are bunched together in helical or wavy configurations, along two spaced paths 141, 142. By using helically configured conductors or wave shaped conductors, both in the substrate 10 and elsewhere in the apparatus, upon flexing of the apparatus, the conductors can effectively expand or contract in length as necessary, avoiding damage to components of the apparatus including the conductors themselves.

The two conductor paths 141, 142 joint together at the proximal end 12 of the substrate 10, adjacent an exit point of the conductors from the substrate 10. At the exit point, the conductors 14 continue along a single helical path, passing through the anchor device 2 and then extending further on through the lead 3.

Figure 3A:
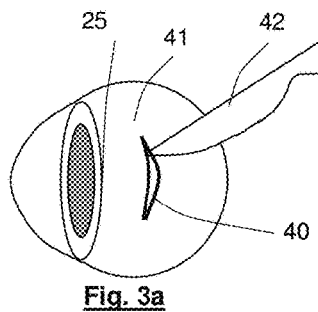
FIGS. 3a to 3c represent example steps for surgically implanting the implantable device of the visual prosthesis apparatus of FIG. 1a in an eye.
Figure 3B:
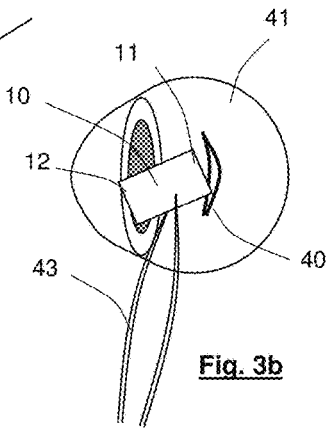
Figure 3C:
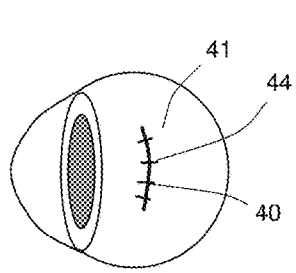
Figure 4A:
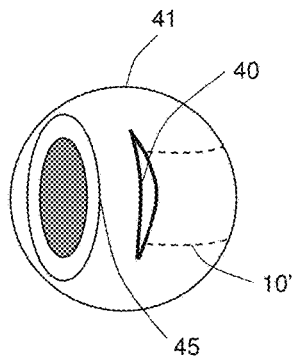
FIGS. 4a and 4b show example positioning of the implantable device of the visual prosthesis apparatus of FIG. 1a relative to the corneal limbus and the optic disk, respectively.
Figure 4B:
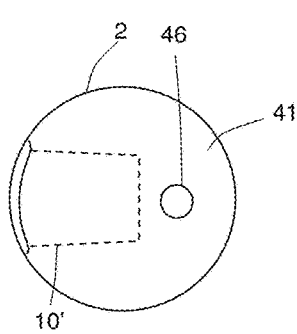

An example method of implanting the substrate 10 in an eye is now discussed with respect to FIGS. 3a to 4b. An incision 40 is made in the sclera 41 of the eye with a scalpel 42, the incision 40 being slightly wider than the width of the substrate 10 (FIG. 3a). The distal end 11 of the substrate 10 is then pushed into the incision, using soft-tipped forceps 43, through the scleral layer and into a pocket between the sclera and the choroid (FIG. 3b). Once fully inserted, the opening of the incision is closed using sutures 44 (FIG. 3c). In this example, as represented in FIGS. 4a and 4b, the incision 40 is about 5 mm from the corneal limbus 45 and the substrate 10, when fully implanted, locates entirely between the sclera and choroid layers of the eye. The electrodes 13 locate adjacent the active cells of the eye's retina, about 2 mm to 4 mm, e.g. 3 mm to one side of the optic disc 46 (in FIGS. 4a and 4b, the location of the substrate 10 under the sclera is indicated by dotted lines 10' and, for simplicity, neither the anchor device 2 nor the lead 3 is represented in FIGS. 3a to 4b).

Figure 5A:
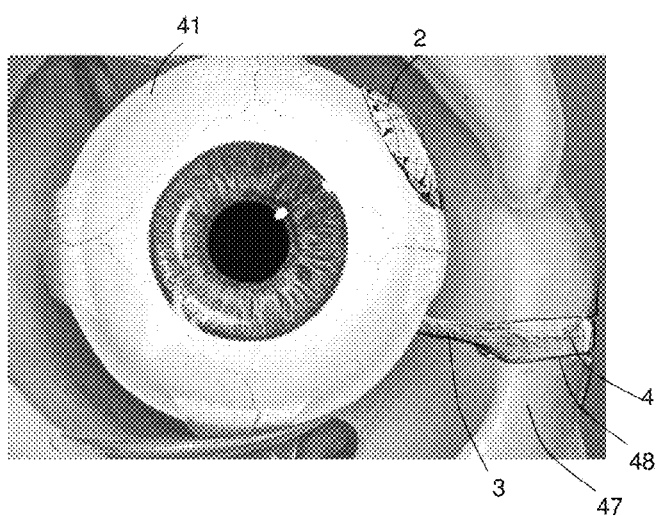
FIGS. 5a and 5b show front and side views of an eye socket with the anchor device and lead of the visual prosthesis of FIG. 1a positioned for use.
Figure 5B:
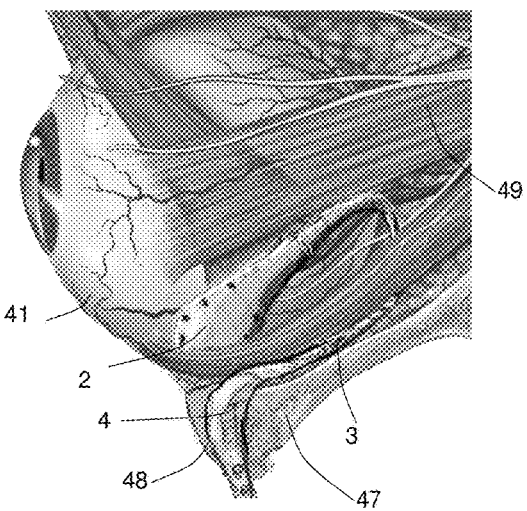

The anchor device 2 is used to stabilise the conductors 14 at the exit point of the eye, prior to routing of the lead 3 towards a communications interface. The anchor device 2 also serves to channel the conductors 14 in an appropriate direction away from the eye, towards the communications interface. FIGS. 5a and 5b show front and top views, respectively, of an eye socket region showing possible location positions for the anchor device 2 in relation to the eye, and routing of the lead 3 from the eye, past the extraocular muscles 49 and around the orbital bone 47 at the lateral orbital margin. The anchor device 2, and indeed the incision 40 where it is located, are strategically positioned on the sclera 41 to avoid interfering with the extraocular muscles 49. Particularly, the incision 40 in this embodiment is positioned behind the connection between the eye and the lateral rectus muscle, and the anchor device 2 is configured to direct the lead 3 rearward, over the top of the lateral rectus muscle and between the lateral rectus muscle and the superior rectus muscle.

Referring again to FIG. 1a, the anchor device 2 includes a fixation portion 21 that is configured to be secured to the sclera of the eye, and a conductor receiving portion 22 having a channel 23 through which the lead 3, which encloses the conductors 14, extends. In this embodiment, the fixation portion 21 and receiving portion 22 are both formed at least in part of silicone, although other flexible polymers or indeed other types of materials may be used.

In one embodiment, the channel 23 can be formed as a direct result of moulding silicone over the lead 3 and/or conductors 14. Alternatively, a channel may be preformed in the receiving portion 22 with the conductors being passed through the channel after forming of the channel. The shape of at least the fixation portion 21 may be varied. For example, it may be extended or widened to provide a larger fixation area.

In this embodiment, the lead 3, while extending through the entire length of the channel 23 of the receiving portion 22, is fixed to the receiving portion 22 adjacent one end of the channel 23 only; in particular, adjacent the end of the channel 202 opposite to the implantable device 1. By fixing the lead 3 adjacent one end only, greater movement of the non-fixed portions of the lead 3 within the confines of the channel 23 is possible. The channel 23 can be sized so that it has a diameter larger than the diameter of the lead 3, allowing greater movement. To this end, gaps can exist between the lead 3 and the channel walls. The gaps may be filled with body fluid during use.

The fixation portion 21 includes a relatively flat piece of silicone in which a layer of polyethylene terephthalate (PET) mesh 24 is embedded, increasing the rigidity and strength of the fixation portion 21. Accordingly, while silicone covering the mesh 24 provides the fixation portion 21 with a relatively conformable surface suitable for engagement with the eye, the size and shape of the fixation portion 21 remains substantially fixed by the mesh 24. Thus, the fixation portion 21 provides a firm, relatively flat, platform for engaging and securing the anchor device 2 to the outer surface of the eye.

The conductor receiving portion 22 includes no reinforcing mesh layer in this embodiment and is therefore relatively flexible in comparison to the fixation portion 21. The receiving portion 22 maintains a gap between the channel 23 and the fixation portion 21, and thus provides a relatively flexible transition region between the channel 23, including the lead and conductors 14, and the fixation portion 21, allowing a controlled degree of movement therebetween. The movement can ensure that, while the anchor device 2 provides a secure path for the conductors 14 to exit the incision 40 in the eye, the conductors 14 may still flex, e.g. during rotation of the eye, reducing the likelihood of damage to the eye at the exit point, or possible breakage occurring to the conductors 14.

Figure 2A:
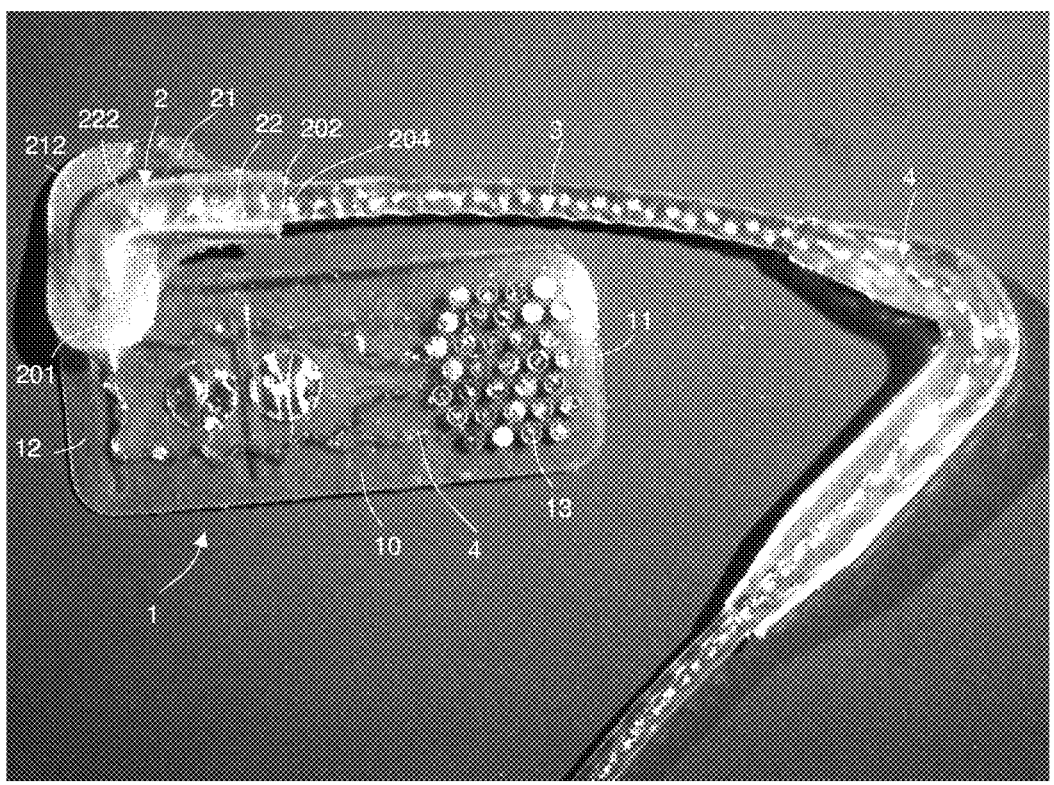
Figure 2B:
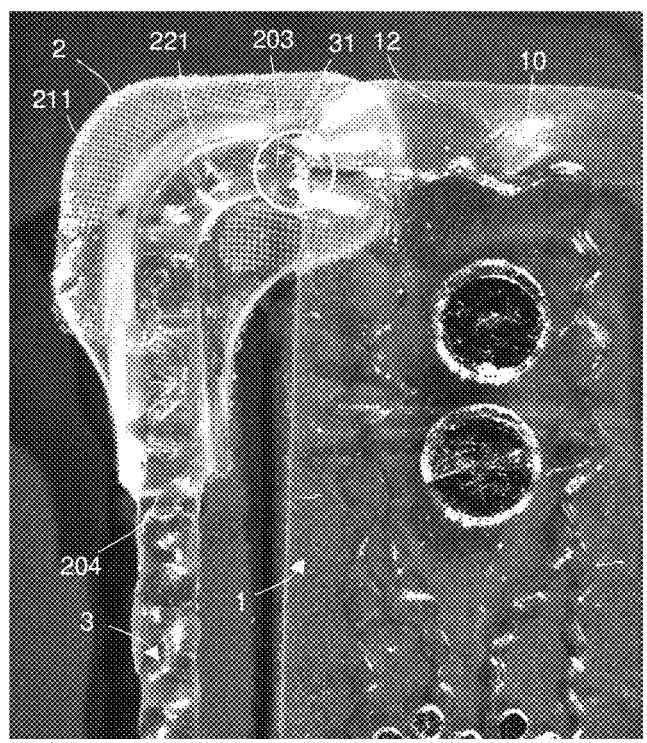

Referring to FIG. 2b, the bottom surface 221 of the receiving portion 22 is substantially flush with the bottom surface 211 of the fixation portion 21 to ensure that a reliable contact between the anchor device 2 and the eye can be achieved with relatively even force distribution across the anchor device 2. The bottom surfaces 211, 221 are curved to follow substantially the curvature of the outer surface of the sclera of the eye. Referring to FIG. 2a, the top surface 222 of the receiving portion 22 protrudes further than the top surface 212 of the fixation portion 21 to accommodate the channel 23 and the lead 3/conductors 14.

In this embodiment, the conductor receiving portion 22 and the channel 23 follow a bent, substantially right-angled, path between a first end 201 of the anchor device 2 adjacent the substrate 10 and a second end 202 of the anchor device 2 where the lead extends from the anchor device 2 towards the communications interface. The conductor receiving portion 22 and channel 23 extend right up to the second end 202 of the anchor device 2, where the channel 23 has a second opening 204 through which the lead 3/conductors 14 exit the channel. However, the conductor receiving portion 22 has an opposite first opening 203 (see FIG. 2b), through which the lead 3/conductors 14 enter the anchor device 2, from a position adjacent the substrate 10, that is set back from the first end 201 of the anchor device 2 and that is provided in the bottom surface 221 of the conductor receiving portion 22. This allows the fixation portion 21 to provide for increased support adjacent the incision 40 in the eye by extending around the conductor receiving portion 22 on three of its sides. It also allows the first opening 203 to lie against the sclera of the eye so that the conductors 14 can enter the anchor device 2 directly from the incision in the eye, permitting sealing or shielding to be achieved at this position.

The apparatus comprises a transition portion between the anchor device 2 and the implantable component 1. In particular, the lead 3 has a section, described herein as a transition lead section 31 and which is circled in FIG. 2b, that extends between a position of the substrate 10 at which the conductors 14 exit the substrate 10 and the first opening 203 of the anchor device 2. The length of the transition lead section 31 corresponds substantially to a thickness of tissue/the length of the incision through which the lead 3 extends from the substrate and exits the eye.

The transition lead section 31 tapers towards the substrate 10 and thus provides a relatively flexible section of the lead adjacent the substrate 10. The transition lead section 31 therefore provides a flexible transition portion between the implantable component 1 and the anchor device 2, and the anchor device 2 can therefore be less likely to impede or obstruct implantation of the implantable component. The flexibility of the transition portion may allow for increased relative movement between the anchor device 2 and the implantable component 1 during the implantation process, minimising any potentially obstructive forces being transferred from the anchor device 2 to the implantable component 1 via the transition portion.

Figures 9A, 9B:
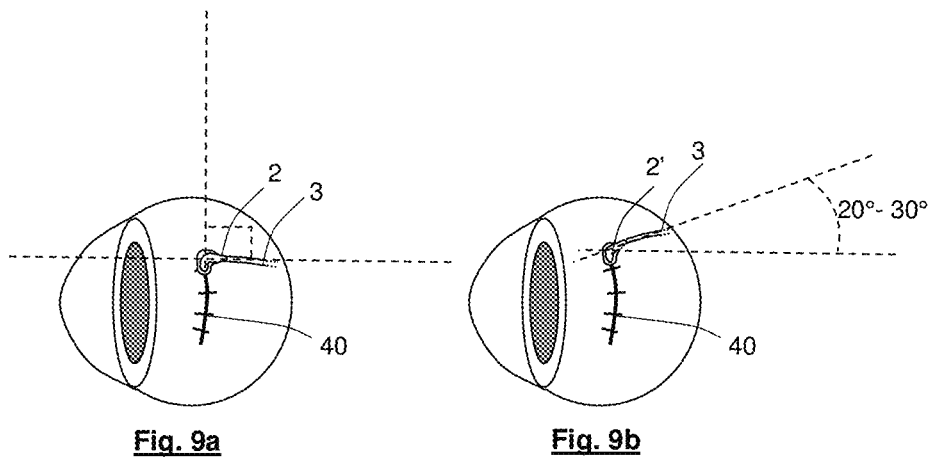
FIGS. 9a and 9b show routing of the lead at the surface of the eye using an anchor device in accordance with FIG. 1a and FIG. 6a, respectively.

In the embodiments described above with reference to FIGS. 1a to 2b, the conductor receiving portion 22 and the channel 23 of the anchor device 2 follow a bent, substantially right-angled path between a first end 201 of the anchor device 2 adjacent the substrate 10 and a second end 202 of the anchor device 2 where the lead extends from the anchor device 2 towards the communications interface. However, with reference to FIGS. 6a and 6b, in an alternative embodiment, an anchor device 2' can be provided in which the conductor receiving portion 22' and the channel can follow a bent path than is not right angled. For example a path may bend by only about 50° to 60°. It has been determined that this can allow the lead 3 to be optimally routed away from the opening in the outer surface of the eye, towards the communications interface, in consideration of the location of the communications interface and the position of anatomical features such as the extraocular muscles. FIGS. 9a and 9b depict the different routes that can be taken by the lead 3 from the incision in the eye 40, towards the communications interface, when channel bends of about 90° and about 50° to 60° are employed in the anchor device 2, 2', respectively. By providing these channel bends, the lead can be routed substantially horizontally across the eye from the anchor device or angled upwardly from horizontal at an angle of about 20° to 30°.

Figure 6A:
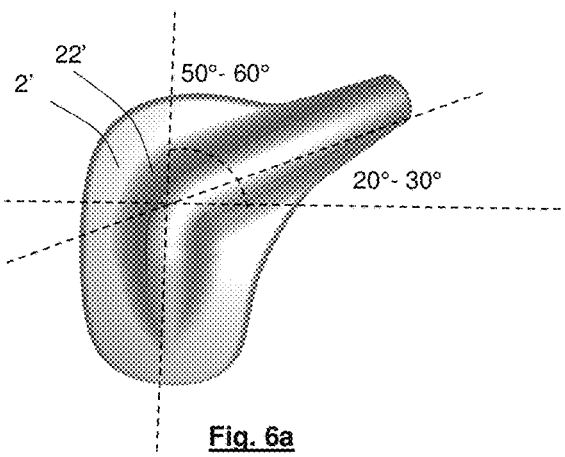
FIGS. 6a and 6b show top and oblique views, respectively, of an anchor device according to an alternative embodiment of the present disclosure.
Figure 6B:
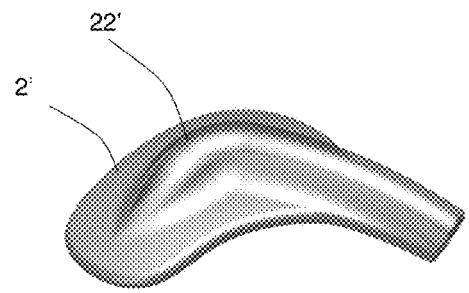
Figures 7A, 7B, 7C:
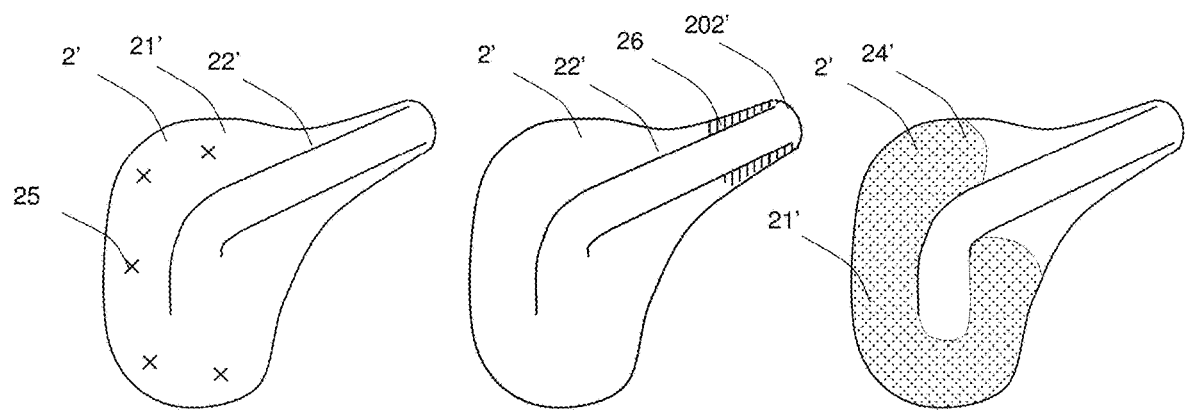
FIGS. 7a to 7c each show a top view of the anchor device of FIG. 6a in which the positioning, with respect to the device, of sutures, glue, and mesh, respectively, is indicated.

FIGS. 7a to 7c each show a top view of the device of FIG. 6a in which the positioning, with respect to the device, of sutures, glue, and mesh is indicated. In more detail, FIG. 7a shows possible connection positions 25 for sutures, which sutures may be used to fix the fixation portion 21' of the device 2' to the outer surface of the eye. The suture connection positions 25 on the fixation portion 21' may be reinforced. FIG. 7b shows positions at which glue 26 (or other fixation means) may be used to connect the lead within the channel of the conductor receiving portion 22'. The lead is fixed adjacent the end 202' of the channel that is opposite to the implantable device, and is fixed along a relatively small percentage of the length of the channel, e.g. less than 50%, less than 40% or less than 30% of the length of the channel. As discussed above, by fixing the lead adjacent one end only, greater movement of the non-fixed portions of the lead within the confines of the channel is possible. FIG. 7c shows location positions for the mesh 24' used to stiffen/reinforce the fixation portion 21'. The positioning and shape of the mesh 24' may allow improved progressive 3-dimensional strain relief on the entry point for the lead into the anchor device 2'. The mesh 24' is tapered to minimise stress at this point.

Figure 8:
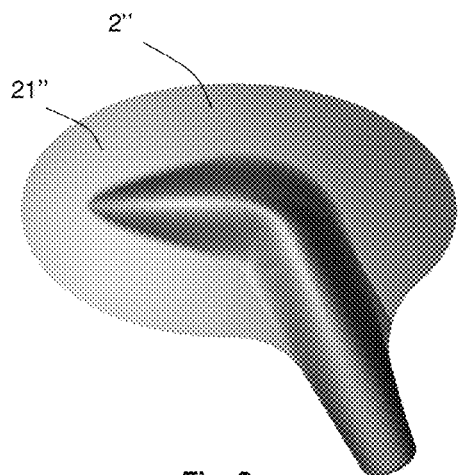
FIG. 8 shows a top view of an anchor device according to an alternative embodiment of the present disclosure.

FIG. 8 shows a top view of an anchor device 2" according to an alternative embodiment of the present disclosure. The anchor device 2" is similar to the anchor device 2' described with reference to FIGS. 6a to 7c. However, the fixation portion 21" of the device has been extended to support increased torsional forces that may result from use of a stiffer lead, for example.

Figure 11:
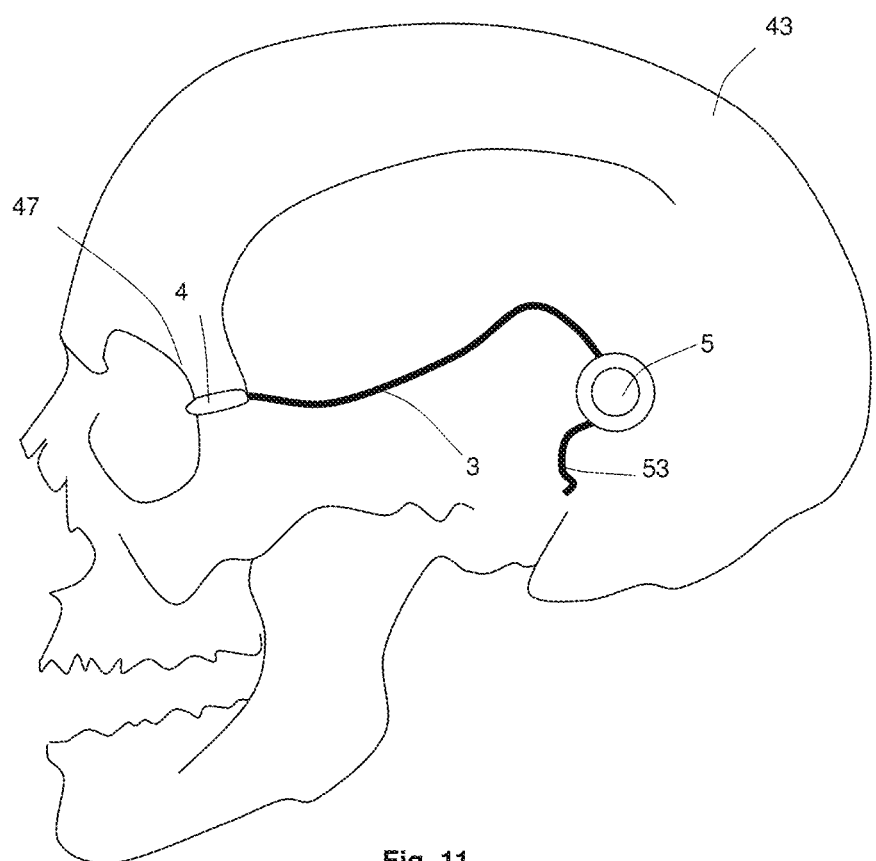
FIG. 11 shows routing of the lead of the visual prosthesis apparatus of FIG. 1a relative to a skull.

The lead 3 includes silicone cladding that surrounds the helically arranged conductors 14. Referring to FIG. 1a, at approximately 3 to 4 cm along the lead from the substrate, the lead 3 is provided with a reinforcement device, referred to hereinafter as a "grommet" 4, that both directs the conductors 14 around the orbital bone 47 of the eye socket, as shown in FIGS. 5a and 5b, and provides protection for the conductors 14 against high stresses at this region. After extending around the orbital bone 47, the lead 3 extends along the side of the patients skull 43 to a communications interface (plug pedestal 5 in this embodiment), as shown in FIG. 11. A return electrode 53 is connected to the pedestal 5.

The grommet 4 has a bend region 402, a first section 401 on the implantable device side of the bend region 401, and a second section 403 on the communications interface side of the bend region 402. A channel extends through the first and second sections 401, 403 and the bend region 402 in which the lead 3/conductors 14 are located. The first section 401 has a length of approximately 0.5 cm and the second section 403 has a length of approximately 1.2 cm. The bend region 402 maintains an angle between the first and second sections 401, 403 of e.g. 63°.

Figure 10:
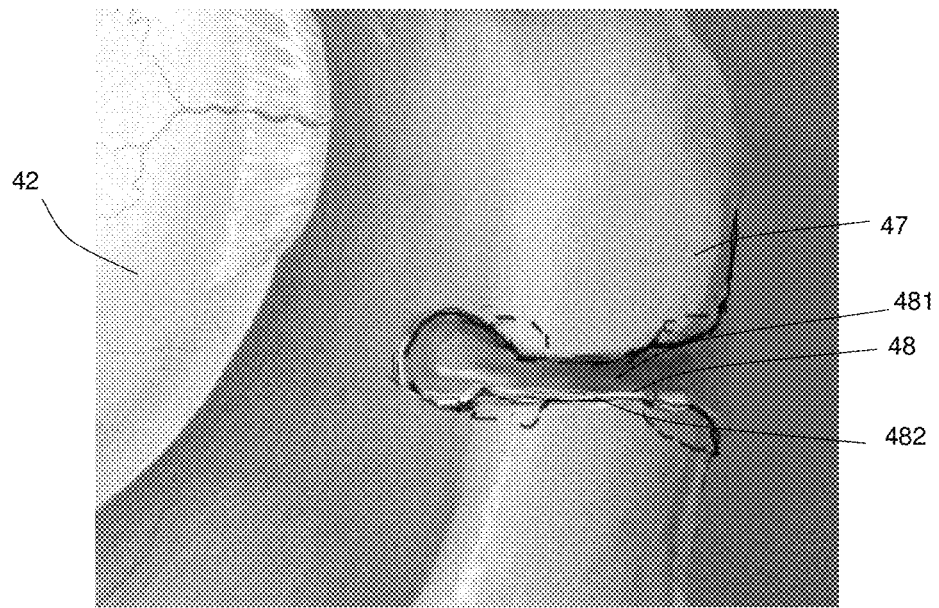

With reference again to FIGS. 5a and 5b, and to FIG. 10, the grommet 4 is configured for location in a notch 48 that is formed in the orbital bone 47 by the surgeon. The notch 48 has a recessed groove 481, arranged to receive the grommet 4, that is formed wider than an access opening 482 to the groove 481. This allows the grommet 4 to be press-fit through the opening 482 into the groove 481, reducing the likelihood that the grommet 4, when located in the groove 481, will be displaced from the groove 481. A dummy device may be used to assist a surgeon with sizing of the notch 48 including the recessed groove 481 and the access opening 482, which dummy device may have substantially the same shape and dimensions as the grommet 4, at least at regions of the grommet 4 that are to be located in the notch 48. The dummy device may be included in a surgical pack, along with one or more of the other items discussed herein, such as the anchor device, grommet, and lead, etc.

Figure 1B:
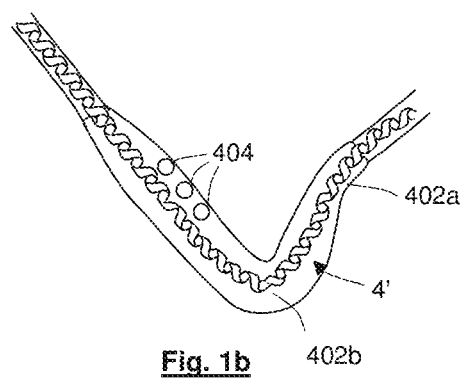

In an alternative embodiment as shown in FIG. 1b, a grommet 4' may be provided having more than one bend. For example, it may have a first bend region 402a and a second bend region 402b. The bends at regions 402a and 402b are in different directions and are appropriate for navigating the orbital bone and enabling the lead to project off the bone surface. The second bend 402b may direct the lead upwards by about 20°, for improved intraorbital lead fit in patients. In other embodiments, the grommet may have 3 or more bend regions. Additionally, the grommet 4' can have one or more lugs 404 to help achieve pressure fitting in the groove 481. The lugs 404 can project from opposite sides of the grommet 4'.

Apparatus for positioning components of the visual prosthesis apparatus, e.g. as shown in FIGS. 1a to 9b and 11, is now discussed with respect to FIGS. 12 to 15.

The apparatus comprises an elongate element 61, referred to hereinafter as a "trocar", which is configured to hold, during positioning, an implantable device and a lead connected to the implantable device, and optionally an anchor device and reinforcement device. The implantable device, anchor device, lead and reinforcement device may be configured in accordance with the implantable device 1, anchor device 2, 2', 2", lead 3, and reinforcement device 4, described above with respect to FIGS. 1a to 9b and 11 or otherwise.

In this embodiment, positioning involves passing the trocar through a first skin incision remote from the patient's eye, tunnelling the trocar under tissue along the patient's skull, and passing the trocar out of a second skin incision adjacent the patient's eye. By performing these steps, it is possible to locate the implantable device at a position adjacent the patient's eye where the surgeon may take hold of the implantable device for the purposes of surgical implantation. At the same time, the lead that is connected to the implantable device can remain routed under the patient's tissue, along the side of the patient skull, to the first incision, where a communications interface (plug pedestal 5 in this embodiment) is positioned.

The first incision may be made in the posterior temporalis muscle such as to expose a flat section of squamous temporal zone, where the plug pedestal may be secured after the periosteum is dissected, for example. The second incision may be made at the lateral orbital margin, for example.

Figure 12:
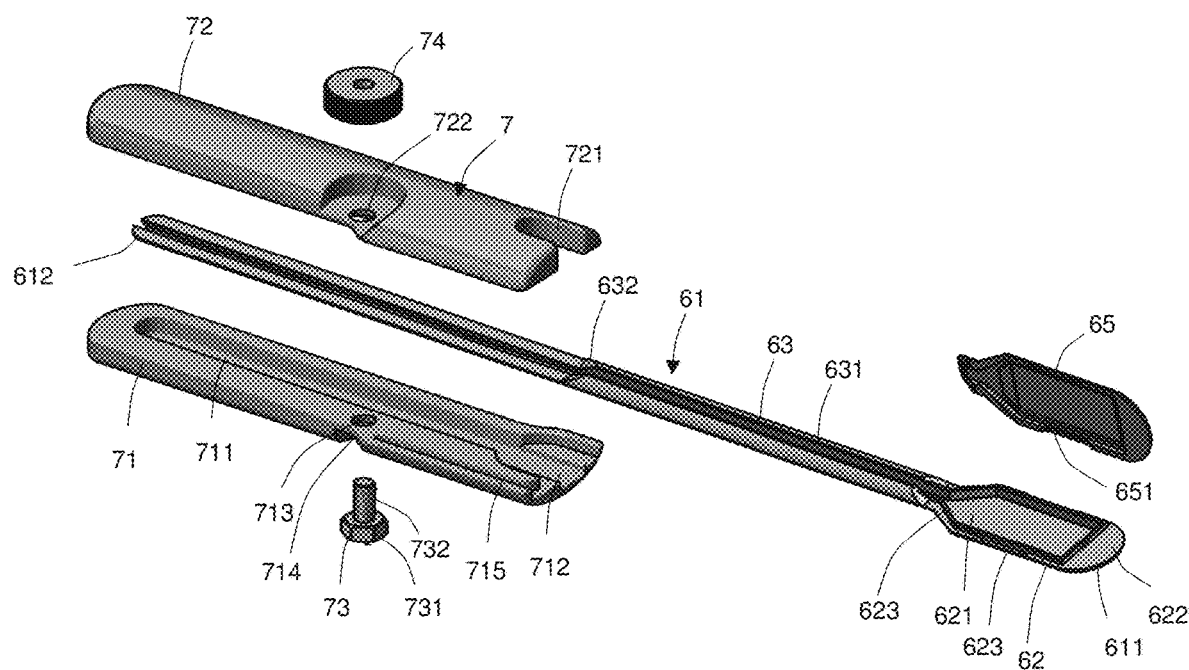
FIG. 12 shows an exploded oblique view of positioning apparatus according to an embodiment of the present disclosure.

Referring to FIG. 12, the trocar 61 includes a head 62 and an arm 63. The head 62 is located at a distal end 611 of the trocar 61, and the arm 63 extends from the head 62 to a proximal end 612 of the trocar 61. The head 62 is substantially wider than the arm 63 and includes a shallow cavity 621 dimensioned to receive the implantable device, and optionally also an anchor device, in a securely packed manner. The arm 63 includes a channel 631 that is open to the cavity 621 and extends proximally along the direction of elongation of the arm 63 to a position about halfway along the length of the arm 63. The channel 631 is configured to receive the lead, and optionally also the reinforcement device, when the implantable device is located in the cavity 621. The length of the channel is such that it can receive a lead having a length that, when located under the skin, provides sufficient slack to allow surgical implantation of the implantable device.

Figure 15:
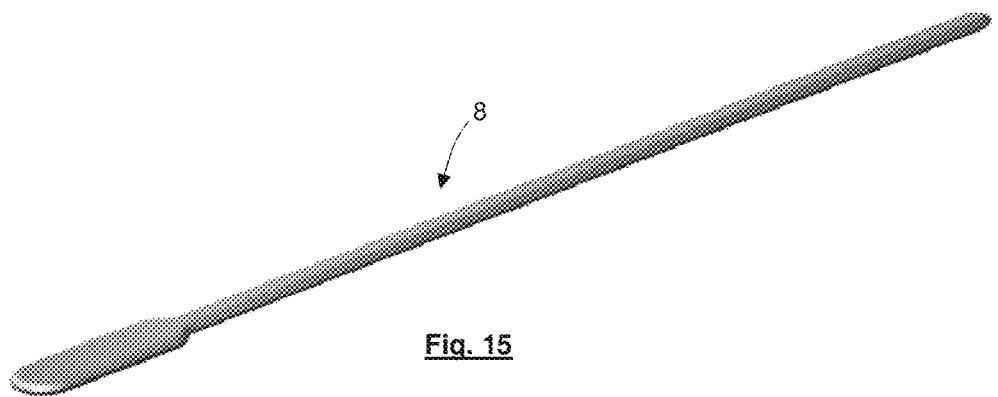
FIG. 15 shows an oblique view of a dummy trocar.

The head 62 provides a leading end to the trocar 61 when it is inserted and tunnelled under the skin. External surfaces of the head 62 are therefore configured in a smooth, streamlined shape to minimise surgical trauma. The streamlined shape is achieved at least through the provision of a curved distal tip 622 to the head 62, through forming the head 62 in a relatively flat configuration, and by providing gently shelving shoulder portions 623 that join the head 62 to the arm 63 without any sharp corners. The flat configuration of the head 62 in particular prevents significant damage occurring to tissue during transfer beneath the skin, since it allows the head 62 to maintain a relatively low profile against the skull while under the skin, prior to it being extended out of the second incision. Nonetheless, prior to insertion of the trocar 61 through the first skin incision, a tunnel may be created from the first incision towards the lateral orbital rim to make transfer of the trocar 61 towards the second skin incision more straightforward. The tunnel may be made beneath the temporalis fascia. The tunnel may be made using a dummy trocar 8 with outer dimensions identical to the implantable device and lead routing trocar 61, as shown in FIG. 15.

Figure 13:
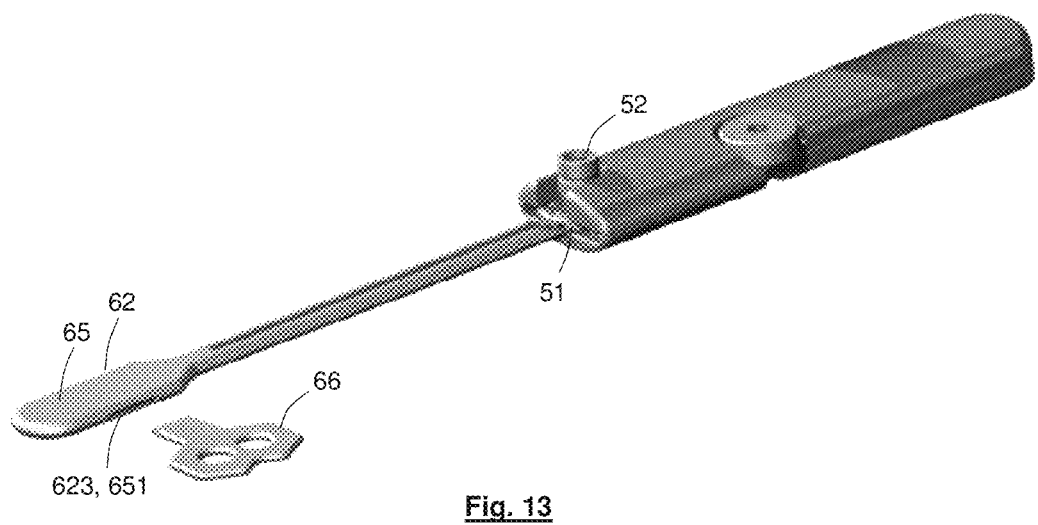
FIG. 13 shows an oblique view of the positioning apparatus of FIG. 12 in a complete state.
Figure 14:
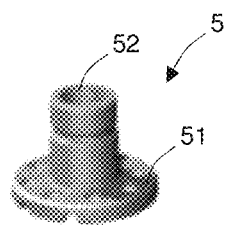
FIG. 14 shows an oblique view of a communications interface locatable in the positioning apparatus of FIG. 12.

To encapsulate the implantable device within the cavity during transfer under the skin, a lid 65 is provided. The lid 65 fits over the cavity 621 and connects to the head 62 around a rim of the cavity 621 in a press-fit manner, generally as shown in FIG. 13. The cavity 621, lid 65 and channel 631 are also configured in a smooth and streamline shape to remove any internal catch points in the trocar 61 that could cause damage to the visual prosthesis components located therein. The cavity 621 is configured such that, when closed by the lid 65, it has ideal packing dimensions for the implantable device located therein.

One or more notches 623, 651 are provided in the head 62 that allow for insertion of a key 66. The key 66 can be turned in the notches 623, 651 to prise open the lid 65, allowing access to the cavity 621 once the head 62 has been extended through the second incision adjacent the eye. Once access is achieved, the surgeon can remove the implantable component from the cavity 621, e.g. using forceps, and manipulate the implantable component for implantation in the patient's eye. While tunnelling under the patient's skin, compressive forces of the skin tissue assist in maintaining the lid 65 in a closed position. The positioning apparatus is formed generally of sufficiently strong and rigid material, e.g. surgical steel, such as to prevent compressive forces damaging the visual prosthesis apparatus.

A handle 7 is positioned at a proximal end region of the arm 63, providing both a grip region for the surgeon to hold when guiding the trocar 61 and a means for retaining the plug pedestal 5. In this embodiment, with reference to FIG. 14, the plug pedestal 5 comprises a base 51 and a boss 52 extending therefrom, and includes electrical contacts for connecting with external electrical components. The plug pedestal 5 is a percutaneous plug pedestal, configured to be located partially under the patient's skin where it is fixed to the patient's skull, e.g. using bone screws such as self tapping screws. Prior to securing, the periosteum may be dissected.

The handle 7 has an ergonomic shape for ease of handling and use and includes first and second handle halves 71, 72 that clamp together on opposite sides of the arm 63 to form the handle, fixing the position of the handle 7 relative to the arm 63 while retaining the plug pedestal 5 at the distal end of the handle 7. When the handle halves 71, 72 are clamped to the arm 63, the arm locates in a retention groove 711 located on an inside surface of the first handle half 71. Furthermore, the base 51 of the plug pedestal locates in a recess 712 at the distal end of the first handle half 71 and abuts against a step 632 in the arm 63 at the proximal end of the channel 631. Meanwhile the boss 52 extends through a relief 721 at the distal end of the second handle half 72. A groove 715 is also provided in the first handle half 71 that receives a return electrode 53 (see also FIG. 11). The clamping arrangement maintains the pedestal 5 and the return electrode 53 in a secure position at an opposite end of the lead 3 to the implantable device, during positioning of the apparatus.

The handle halves 71, 72 are secured together using a bolt 73. The bolt 73 extends through holes 713, 722 provided in each of the handle halves 71, 72. The bolt 73 has a head end 731 that locates in a recess 714 on the outer side of the first handle half 71, and has a threaded body 732 that passes through the holes 713, 722 and engages with a nut 74 located to the outer side of the second handle half 72. The nut 74 is knurled and can be turned relatively easily using the thumb and finger to enable the handle halves 71, 72 to be separated and the handle 7 to be released from the trocar 63. The groove 715 is configured such that, during separation of the handle halves 71, 72, the return electrode 53 is drawn out of the groove, e.g. ready for implantation under skin behind the ear. By allowing for relatively easy release of the handle 7, after the apparatus has been used to transfer the implantable device and lead into position, the trocar 61 can be removed through the second incision at the orbital margin in the same direction as it was moved under the patient's skin from the first incision, without obstruction by the handle (the handle need never be extended under the skin). By pulling the trocar through the second incision at the lateral orbital rim, rather than retracting it back through the first incision adjacent the ear, surgical trauma can be minimised.

While the positioning apparatus and methods described above with reference to FIGS. 12 to 15 are used in conjunction with visual prosthesis apparatus, similar positioning apparatus and methods can be used to position other apparatus that employs electrical and implantable components. For example, similar positioning apparatus and methods can be used in conjunction with apparatus including a component that is implantable in or on the brain. One example of this is apparatus adapted to limit or prevent onset of epileptic seizures, and/or to monitor body parameters associated with epileptic seizures, and which employs an electrode array that is adapted to be placed within or near the source or sources of seizures in the brain. Electrical stimulus can be applied by the electrodes to terminate or at least counteract epileptic seizure events arising from those sources and/or the electrodes can be used to monitor electrical activity within or near the source or sources of seizures in the brain.

Figure 16:
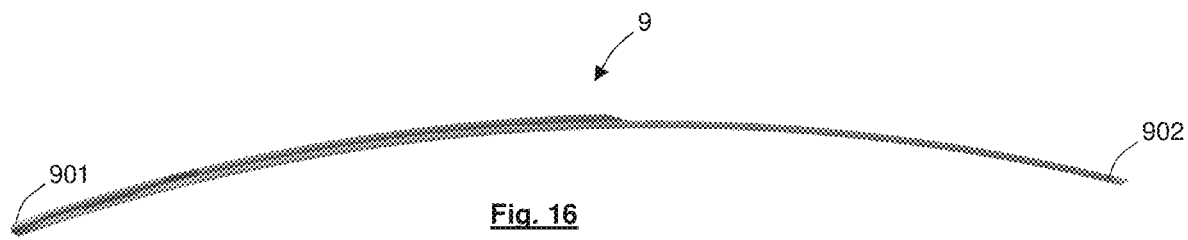
FIG. 16 shows a side view of a trocar according to an alternative embodiment of the present disclosure.
Figure 17:
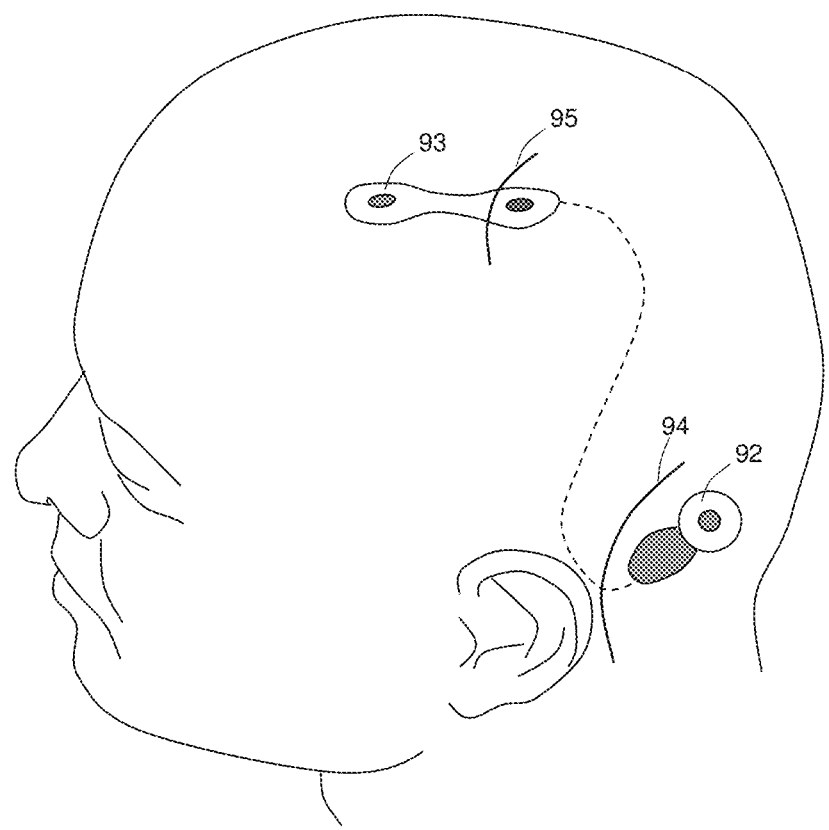
FIG. 17 shows positioning of apparatus components following use of the trocar of FIG. 16.

Referring to FIGS. 16 and 17, such apparatus can employ a trocar 9 (and optionally a corresponding dummy trocar) that is configured in substantially the same manner as described with reference to FIGS. 12, 13 and 15, but which has a head at the distal end 901 with a first recess dimensioned instead to receive an implantable device 91, including a plurality of electrodes, for use with epilepsy treatment, and which trocar is curved to follow the curvature of the skull between an appropriate implantation position towards the top of the skull and a location position for a communications interface 92 (e.g. pedestal).

As before, a handle (not shown) is releasably attached to a proximal end 902 of the trocar 9 and the communications interface 92 is at least partially located in the handle. The implantable device 93 is at least partially located in the first recess adjacent the distal end 901 of the trocar. The trocar has a lead channel extending proximally from the first recess with a lead, that connects between the implantable device and the communications interface, at least partially located in the lead channel. The distal end 901 of the trocar 9 is inserted through a first incision 94 adjacent the ear and tunnelled under tissue towards the target position. The distal end of the trocar 9 is then pushed out of a second incision 95 adjacent the target position and the implantable device is removed from the first recess. The handle is then released from attachment with the trocar 9 and the communications interface is released from the handle. The trocar 9 is pulled out of the second skin incision 95. The implantable device is manually inserted into a tissue pocket under the patient's scalp, sutured in place and the incisions (wounds) are closed.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. Positioning apparatus for positioning components of electrical apparatus, the electrical apparatus including a device implantable at a target portion of a patient's body, an electrical component, and a lead extending between the implantable device and the electrical component, the positioning apparatus comprising:

an elongate element having a proximal end and a distal end, the distal end being insertable through a first incision in a surface of a patient, and movable under tissue towards the target position, and a handle portion releasably attachable to a proximal end region of the elongate element;

wherein the elongate element has a first recess at the distal end adapted to receive the implantable device and a channel extending proximally from the first recess adapted to receive the lead, and wherein the handle includes a second recess adapted to receive the electrical component.

2. The positioning apparatus of claim 1, wherein the electrical apparatus is a visual prosthesis, the visual prosthesis including the implantable device, the device being implantable in an eye, the electrical component, and the lead extending between the implantable device and the electrical component, and wherein:

the distal end of the elongate element is insertable through the first incision in a skin surface of a patient, and movable under tissue towards a patient's eye.

3. The apparatus of claim 2, wherein the distal end of the elongate element is movable under the tissue through a second incision in a skin surface of the patient, the second skin incision being located at or adjacent the lateral orbital margin of the eye socket surrounding the eye.

4. The apparatus of claim 1, wherein the electrical apparatus is adapted to limit or prevent onset of epileptic seizures, and/or to monitor body parameters associated with epileptic seizures.

5. The apparatus of claim 1, wherein the elongate element comprises a head at the distal end that includes the first recess and an arm extending proximally from the head, the arm including the channel, wherein the channel has an opening at its distal end that opens into the first recess.

6. The apparatus of claim 5, comprising a releasable lid for covering the first recess.

7. The apparatus of claim 1, wherein the handle comprises first and second portions configured to releasably clamp together from opposite sides of the arm, fixing the position of the handle relative to the arm.

8. The apparatus of claim 7, wherein the clamping secures the electrical component in the second recess.

9. The apparatus of claim 1, wherein the elongate element is bent to follow contours of a human skull.

10. The apparatus of claim 1, wherein the elongate element is substantially straight.

11. A method of positioning components of electrical apparatus, the electrical apparatus including a device implantable at a target position in a patient's body, an electrical component, and a lead extending between the implantable device and the electrical component, the method comprising:

inserting a distal end of an elongate element through a first incision remote from the target position, wherein the elongate element has:
  a first recess at the distal end, the implantable device being at least partially located in the first recess, and
  a lead channel extending proximally from the first recess, the lead being at least partially located in the lead channel, and wherein
  a handle is releasably attached to a proximal end of the elongate element, the handle including a second recess, the electrical component being at least partially located in the second recess;
moving the distal end of the elongate device under tissue towards the target position;
pushing the distal end of the elongate device out of a second incision adjacent the target position;
removing the implantable device from the first recess;
releasing the handle portion from attachment with the elongate element;
removing the electrical component from the second recess; and
pulling the elongate element out of the second incision.

12. The method of claim 11, wherein the electrical apparatus is a visual prosthesis, the visual prosthesis including the implantable device, the device being implantable in a patient's eye, the electrical component, and the lead extending between the implantable device and the electrical component, wherein:

the first incision is a first skin incision remote from the patient's eye and the second incision is a second skin incision adjacent the patient's eye;
the distal end of the elongate device is moved under tissue towards the patient's eye; and
the distal end of the elongate device is pushed out of the second skin incision adjacent the patient's eye.

13. The method of claim 12, wherein the first incision is in the posterior temporalis muscle and the second incision is at the lateral orbital margin.

14. The method of claim 11, wherein the electrical apparatus is adapted to limit or prevent onset of epileptic seizures, and/or to monitor body parameters associated with epileptic seizures.

15. The method of claim 11, wherein the elongate element comprises a head at the distal end that includes the first recess and an arm extending proximally from the head, the arm including the channel, wherein the channel has an opening at its distal end that opens into the first recess.

16. The method of claim 11, comprising a lid for covering the first recess, wherein the lid is released to remove the implantable device from the first recess.

17. The method of claim 11, wherein the handle comprises first and second portions configured to releasably clamp together from opposite sides of the arm, fixing the position of the handle relative to the arm, wherein clamping of the first and second portions is released to remove the electrical component from the second recess.

18. The method of claim 11, comprising, prior to insertion of the distal end of the elongate element through the first incision, forming a pocket between the first and second incisions using a dummy element.

19. The method of claim 18, wherein the dummy element has a similar or identical profile to the elongate element.

20. The method of claim 11, wherein the elongate element is bent to follow contours of a human skull.

21. The method of claim 11, wherein the elongate element is substantially straight.

* * * * *